(12) United States Patent
Zakai

(10) Patent No.: US 10,660,791 B2
(45) Date of Patent: May 26, 2020

(54) PERSONAL COOLING SYSTEM AND METHOD OF OPERATION

(71) Applicant: Hillel Zakai, Teaneck, NJ (US)

(72) Inventor: Hillel Zakai, Teaneck, NJ (US)

(73) Assignee: Hillel Zakai, Teaneck, NJ (US)

( * ) Notice: Subject to any disclaimer, the term of this patent is extended or adjusted under 35 U.S.C. 154(b) by 41 days.

(21) Appl. No.: 15/701,280

(22) Filed: Sep. 11, 2017

(65) Prior Publication Data

US 2019/0076293 A1 Mar. 14, 2019

(51) Int. Cl.
*A61F 7/02* (2006.01)
*B65D 33/14* (2006.01)
*A61F 7/10* (2006.01)

(52) U.S. Cl.
CPC .............. *A61F 7/02* (2013.01); *A61F 7/0241* (2013.01); *A61F 7/10* (2013.01); *B65D 33/14* (2013.01); *A61F 2007/023* (2013.01); *A61F 2007/0228* (2013.01); *A61F 2007/0249* (2013.01); *A61F 2007/0292* (2013.01); *A61F 2007/108* (2013.01)

(58) Field of Classification Search
CPC ........... A61F 7/02; A61F 13/12; B65D 33/14; A41D 13/0053; F25D 31/007; F25D 3/06; F25D 3/08; C09K 5/063; C09K 5/02; C09K 5/06
See application file for complete search history.

(56) References Cited

U.S. PATENT DOCUMENTS

| | | | |
|---|---|---|---|
| 3,874,504 A | 4/1975 | Verakas | |
| 4,604,987 A | 8/1986 | Keltner | |
| 5,716,388 A | 2/1998 | Petelle | |
| 6,893,453 B2 | 5/2005 | Agarwal et al. | |
| 7,234,458 B2 | 6/2007 | Takeuchi et al. | |
| 7,517,013 B1 | 4/2009 | Lowe | |
| 8,556,337 B1 | 10/2013 | Cornitius-Cary | |
| 9,549,617 B1 | 1/2017 | Deluca | |
| 2005/0049662 A1 | 3/2005 | Purcell | |
| 2005/0183446 A1* | 8/2005 | Fuchs | A45C 11/20 62/457.7 |
| 2008/0164265 A1* | 7/2008 | Conforti | B65D 81/3823 220/592.2 |
| 2009/0301119 A1* | 12/2009 | Chen | F24F 5/0007 62/235.1 |
| 2013/0015083 A1* | 1/2013 | Seagle | B65D 19/18 206/216 |
| 2013/0289680 A1* | 10/2013 | Hasegawa | A41D 13/0058 607/112 |
| 2016/0113422 A1* | 4/2016 | Huffar | G07F 9/105 705/23 |
| 2017/0303607 A1* | 10/2017 | Iser | A41D 13/0053 |

FOREIGN PATENT DOCUMENTS

KR 20140141161 A * 12/2014

* cited by examiner

*Primary Examiner* — Emmanuel E Duke
(74) *Attorney, Agent, or Firm* — Taft Stettinius & Hollister LLP

(57) ABSTRACT

A personal cooling system for maintaining an individual at a preferred predetermined temperature in the outdoor environment of a venue, for an extended period of time, according to one embodiment includes a first cooling element comprising a phase change material (PCM) and at least one cooling station for providing any one of an additional one or more frozen cooling elements, each having a PCM, and at least one freezing medium for freezing any of said cooling elements. The cooling station is installed at the venue.

22 Claims, 5 Drawing Sheets

PERSONAL COOLING SYSTEM AND METHOD OF OPERATION

FIELD OF THE INVENTION

The present invention relates to the field of outdoor cooling. In particular, the present invention relates to personal cooling in an outdoor environment. More particularly, the present invention relates to a system and method for providing a personalized cooling solution to a plurality of people with different cooling temperature preferences.

BACKGROUND OF THE INVENTION

When travelling outdoors during certain times of the day, as well as in seasons and climates in which temperatures are excessively high, it is important for the body to maintain a suitable temperature level to avoid dangerous health consequences associated with overheating, as well as to preserve bodily comfort throughout the day. A number of methods have traditionally been used in order to deal with this issue, however, none of them have been able to provide a complete cooling solution.

Wearing lightweight clothing provides only partial relief from an environment having consistently high and/or rising temperatures for an extended period of time. Portable air conditioning units and fans are often impractical for a variety of reasons, including bulkiness, lack of accessible electricity and mobility issues. Frozen ice packs overcome the deficiencies described above, however, they melt quickly, especially in the hot environment in which they are typically needed. These ice packs maintain their cold temperature for only a limited amount of time (typically well short of the duration of the outdoor excursion), after which they melt and become a burden to transport. As well, they can leave frostbite or ice burn on the skin of some individuals. Re-freezing is also generally not an option since a freezer is normally not nearby, and even if a freezer were to be found, it would take close to, if not more than an hour to re-freeze the ice pack (depending on size), causing significant time delays in the planned activities. Additionally, different people consider themselves at different levels of discomfort in high temperature environments, therefore, they would naturally prefer different levels of cooling to return to their desired state of comfort. Frozen ice packs, however, provide a standardized freezing temperature which don't take into account these varying preferences. Also, an individual might desire different temperatures for comfort throughout the day depending on factors such as changes in weather, cloud positions, or simply the amount of time that he or she has been in contact with the ice pack. Related solutions, such as cooling vests, which have one or more compartments containing phase change materials (PCM) in a frozen state, as well as other PCM cooling products for cooling a portion of the body, have similar shortcomings as described with respect to frozen ice packs.

It is recognized that a comprehensive solution to the problems described above would benefit people who find themselves in a variety of outdoor venues. Such venues include, for instance, amusement/theme parks, carnivals, music festivals, stadiums, sporting events, beaches, public and hotel pools, hiking trails, parks, and outdoor tourist attractions.

In addition to the above mentioned known partial solutions, the following are other attempts at providing personal outdoor cooling relief.

By way of example, a company known as Black Ice (blackicecooling.com) sells a variety of wearable cooling products for reducing pain and swelling to different parts of the body, such as the neck, wrist, knee, shoulder and back. The products comprise phase change material that freezes to a temperature of 52 degrees Fahrenheit. Additionally, they sell personal cooling products such as neck collars and bandanas, comprising phase change material that freezes to a temperature of 57 degrees Fahrenheit. They claim that their personal cooling products can take as little as 20 minutes to freeze in an ice water bath and can maintain their 57 degree temperature for up to an hour and a half. Black Ice recommends carrying around extra products in an ice cooler to maintain cool relief throughout the entire day. This can be burdensome and impractical for many of the outdoor venues listed above. Moreover, a product that freezes at a single temperature will not provide appropriate cooling relief to a plurality of people who might be travelling together, each having different cooling preferences. Furthermore, much like majority of PCMs in the market the Black Ice products do not melt and freeze at the precise temperature as claimed, rather, within a range of freezing temperatures (that may shift over time) having a deviation of approximately 2 degrees in either direction. Black Ice, like other PCM based products, does not overcome all of the above stated issues and limitations with traveling outdoors in the heat.

Some patent documents disclose yet additional partial solutions to the difficulties associated with outdoor venues in high temperatures, such as the following.

U.S. Pat. No. 8,556,337 to Cornitius-Cary discloses a removable thermal cooling/heating seat/backrest cover having a generally rectangular rear panel formed of flexible water-resistant material, and a front panel including at least one large generally rectangular thermally insulated pocket having an outer side wall formed of a flexible sheet of water and mildew resistant material with an inner side wall formed of shiny reflective metalized foil laminated to closed cell polyethylene foam, the foil facing the interior of the pocket, and the foam facing the rear panel. The cover is removably mounted on the backrest and/or seat of a seating structure by mounting straps. The thermally insulated pocket holds a freezable or microwaveable gel pack for providing cooling or heating comfort to a user. The foil forms a reflective thermal barrier that radiates cold or hot temperatures toward the outer side wall and the foam facilitates maintaining the gel pack at a constant temperature.

This thermal seat cover provides little benefit to the user after a short amount of time once the freezable gel pack melts. Similar drawbacks as mentioned with respect to the Black Ice products, such as uniform freezing temperature, and others, are also applicable to the '337 document.

Other patent documents with at least one or more of the same drawbacks mentioned above with respect to the known partial solutions include: U.S. Pat. Nos. 9,549,617, 5,716,388, 20050049662, 6,893,453, 4,604,987, 3,874,504, 7,517,013 and 7,234,458.

It is not known of any comprehensive cooling system that provides frozen cooling packs to a plurality of people with different cooling preferences and enables them to keep cool for an extended period of time, throughout the day, while in an outdoor venue.

Accordingly, it is a principal object of the present invention to provide a personal cooling system and method for operating the cooling system, that overcomes the difficulties and drawbacks associated with the prior art solutions as described in part herein above.

It is a further object of the present invention to provide a cooling system that takes into account extensive stays in an outdoor environment.

It is an additional object of the present invention to provide a cooling system that is functionable in a variety of outdoor venues.

It is another object of the present invention to provide a cooling system that takes into account different cooling preferences of different people.

It is yet another object of the present invention to provide a cooling system that enables the user to choose his preferred cooling temperature.

Additional objects and advantages of the present invention will become apparent as the description proceeds.

SUMMARY OF THE INVENTION

In accordance with a preferred embodiment of the present invention, a personal cooling system for maintaining an individual at a preferred predetermined temperature in the outdoor environment of a venue, for an extended period of time wherein the system comprises a first cooling element comprising a phase change material (PCM), and at least one cooling station for providing any one of: an additional one or more frozen cooling elements, each comprising a PCM, and at least one freezing medium for freezing any of the cooling elements. The cooling station is installed at the venue.

Preferably, at least one of the cooling elements is insertable into a pocket for attaching to a seat, wherein the pocket comprises straps, clips or any alternative attaching means for attaching to a seat.

At least one or more insulating sheets are preferably provided for removably placing between the cooling element and the individual. The pocket is mounted over a seat by hanging the one or more insulating sheets over the seat back.

One or more insulating sheets are provided for removably placing between the pocket and the individual. The one or more insulating sheets are optionally attached to the pocket.

The cooling station is preferably transportable.

The cooling station is preferably installed at a venue.

The system comprises a network of cooling stations situated separately at predetermined locations.

Preferably, the cooling station provides additional one or more frozen cooling elements for a fee. The cooling station is optionally comprised of a vending machine.

The freezing medium is chosen from one of ice, ice packs and hydratable ice sheets. The freezing medium optionally comprises an environment whose temperature is below the freezing temperature of the PCM it is freezing. Optionally, the freezing medium is a liquid that is kept in the liquid state, below the freezing temperature of the PCM submerged within it. Optionally, the freezing medium is a mixture of water and one of salt and alcohol that is kept at a low temperature, such as at a temperature range between −3 and −25 degrees Celsius.

Optionally, the freezing medium serves as a disinfectant to sanitize the cooling element from bacteria and other microbes.

The personal cooling system further comprising a cleaning material for disinfecting the cooling element from bacteria and other microbes.

The present invention further comprises a personal cooling system for maintaining an individual at a preferred predetermined temperature in an outdoor environment for an extended period of time, where the system comprises a first cooling element comprising a phase change material (PCM), and at least one cooling station for providing any one of: an additional one or more frozen cooling elements, each comprising a PCM, and at least one freezing medium for freezing any of the cooling elements, wherein the cooling elements are designed to be wearable around at least a portion of the neck of a user.

Preferably, the freezing temperature of the PCM of at least one of the cooling elements is different from the freezing temperature of the PCM of at least one other of the cooling elements.

The cooling element preferably comprises a transparent enclosure in which the PCM is contained, for viewing the phase state of the PCM.

The freezing temperature of the PCM is a range of temperatures, and the cooling element comprises a visual indicator for indicating the freezing temperature range of the PCM.

The visual indicator comprises the PCM having a predetermined color, chosen to correspond to the freezing temperature range of the PCM. A list of colors and their corresponding range of freezing temperatures is preferably displayed to a user. The visual indicator optionally comprises an indicative symbol such as numeral and textual.

The cooling element is preferably wearable on the skin.

The freezing temperature of each PCM is a range of temperatures.

Preferably, the cooling station is transportable and optionally is installed at a venue.

The system preferably comprises a network of cooling stations situated separately at predetermined locations. Preferably, the cooling station provides additional one or more frozen cooling elements for a fee. Optionally, the cooling station is comprised of a vending machine.

Optionally, the freezing medium is chosen from one of ice, ice packs and hydratable ice sheets. The freezing medium optionally comprises an environment whose temperature is below the freezing temperature of the PCM it is freezing. The freezing medium is optionally a liquid that is kept in the liquid state, below the freezing temperature of the PCM submerged within it. The freezing medium is optionally a mixture of water and one of salt and alcohol that is kept at a low temperature, such as at temperature range between −3 and −25 degrees Celsius.

Optionally, the freezing medium serves as a disinfectant to sanitize the cooling element from bacteria and other microbes The personal cooling system optionally further comprises a cleaning material for disinfecting the cooling element from bacteria and other microbes.

Preferably, the personal cooling system comprises an app for providing the individual information about nearby cooling stations. The app provides a user with a unique identifier that entitles to recharge or swap cooling elements.

The present invention further comprises a personal cooling element for maintaining an individual at a preferred predetermined temperature in an outdoor environment, the cooling element comprising a transparent enclosure in which a phase change material (PCM) is contained, for viewing the phase state of the PCM, and wherein the freezing temperature of the PCM is a range of temperatures and wherein the cooling element comprises a visual indicator for indicating the freezing temperature range of the PCM.

The visual indicator preferably comprises the PCM having a predetermined color, chosen to correspond to the freezing temperature range of the PCM. The list of colors and their corresponding range of freezing temperatures is preferably displayed to a user. The visual indicator comprises an indicative symbol such as numeral and textual. The cooling element is designed to be wearable. The cooling element is insertable to a pocket for attaching to a seat.

The present invention further comprises a method of supplying cooling elements to a plurality of individuals to stay cool for a significant duration of time outdoors, the method comprising the following steps:

a. providing one or more cooling stations, wherein each cooling station is installed at a venue and comprises at least one freezing medium for freezing a plurality of cooling elements, wherein each cooling element comprises a phase change material (PCM);

b. situating the one or more cooling stations at predetermined locations accessible to the plurality of individuals;

c. supplying the plurality of individuals with cooling elements from the one or more cooling stations, wherein each of the cooling elements has a PCM with a predetermined freezing temperature;

d. optionally transferring one or more melted cooling elements by the one or more individuals to the cooling station for re-freezing at the cooling station; and optionally swapping for a different cooling element to extend duration of cool outdoors or for a different temp.

To accomplish the above and related objects, the invention may be embodied in the form illustrated in the accompanying drawings. With specific reference now to the figures in detail, it is stressed that the particulars shown are by way of example and for purposes of illustrative discussion of the preferred embodiments of the present invention only and are presented in the cause of providing what is believed to be the most useful and readily understood description of the principles and conceptual aspects of the invention. In this regard, no attempt is made to show details of the invention in more detail than is necessary for a fundamental understanding of the invention, the description taken with the attached figures making apparent to those skilled in the art how the several forms of the invention may be embodied in practice.

DETAILED DESCRIPTION

Figure 1:
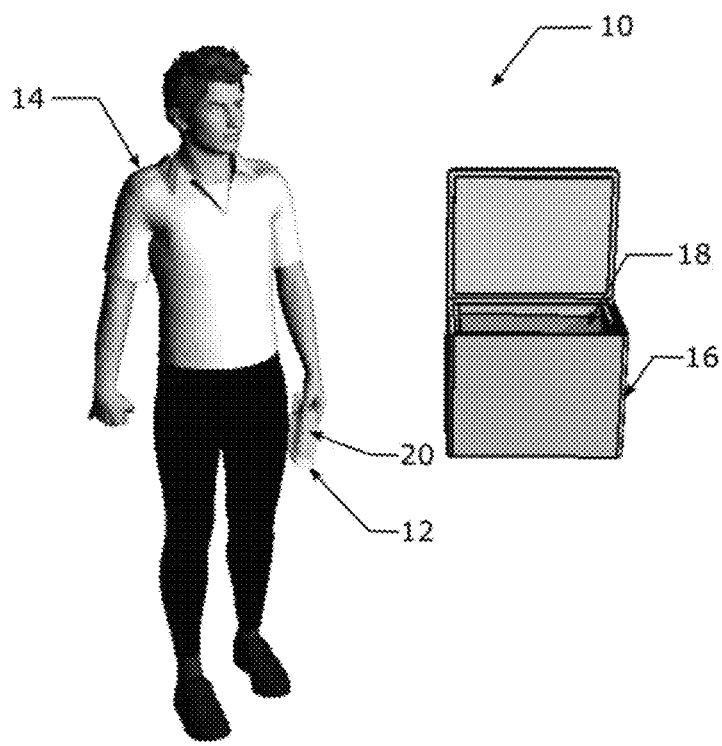
FIG. 1 shows a first aspect of cooling elements of the present invention, and a cooling station of the present invention in a schematic view.

A first preferred embodiment of the personal cooling system of the present invention is shown in FIG. 1 in a schematic view designated generally by numeral (10), comprising a cooling element (12) being held by an individual user (14) for cooling at least part of the external surface of the body of user (14) (e.g. neck, back, etc.) to a preferred predetermined temperature, and also comprising a cooling station (16) having a freezing medium (18) for freezing one or more cooling elements (12). Cooling elements (12), having a phase change material (20) within, are provided to user (14) from cooling station (16), and user's (14) cooling elements (12) are re-frozen or swapped at cooling station (16) as desired.

Figure 2:
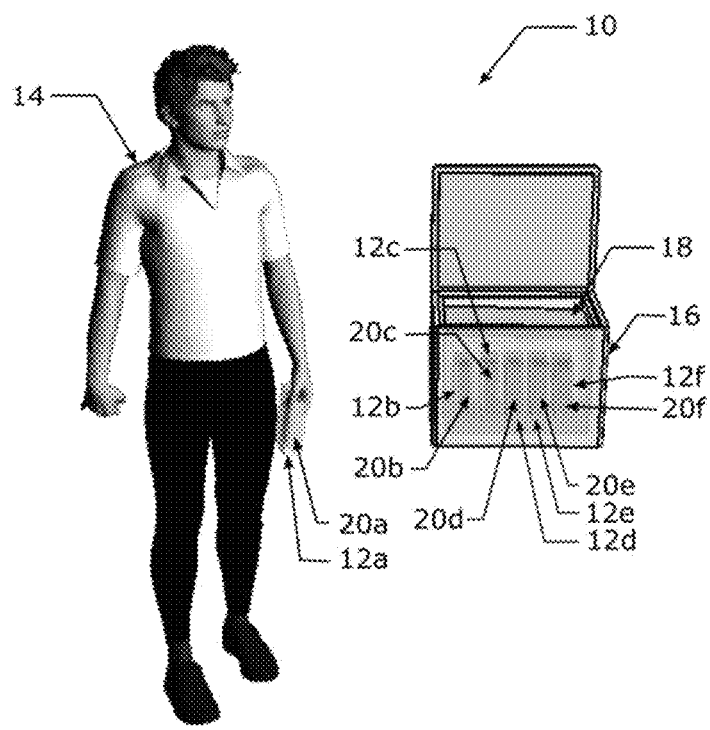
FIG. 2 shows the view of FIG. 1, wherein multiple cooling elements of FIG. 1 are differentiated by their predetermined freezing temperatures.

Referring now to FIG. 2, personal cooling system (10) is shown with cooling station (16) providing multiple cooling elements (12a-f) having PCMs (20a-f).

Although cooling station (16) is shown in the figure with six cooling elements (12a-f) designed according to a first aspect of the first embodiment of the present invention, it is understood that this is just an example for purposes of illustration, and in some cases of the preferred embodiment, cooling station (16) may have fewer or greater than the six cooling elements (12a-f) shown in the figure. Moreover, although cooling station (16) is shown with a single compartment for freezing and re-freezing cooling elements (12a-f), it is understood that in some embodiments cooling station (16) comprises a first compartment for freezing and re-freezing cooling elements (12a-f) and a separate insulated compartment (not shown) for maintaining frozen cooling elements (12a-f) in their frozen state.

Each cooling element (12a-f) comprises a phase change material (PCM) (20a-f) having a predetermined freezing temperature. In some cases, the PCMs of the different cooling elements (12a-f) provided by cooling station (16) have the same temperature as each other. However, in other cases, for reasons related to personal preference, as described herein above, cooling station (16) provides at least two cooling elements, wherein the PCM of a first cooling element has a different freezing temperature than the PCM of a second cooling element.

Multiple cooling elements (12a-f) are identical in their structural components, however, in cases where cooling elements (12a-f) have different freezing temperatures, user (14) is capable of determining the different predetermined freezing temperatures of the different cooling elements (12a-f) due to the following two features: Each cooling element (12a-f) comprises a transparent enclosure material, for instance, see-through plastic, in which its corresponding PCM (20a-f) is contained; and, each PCM (20a-f) has a unique color corresponding to its unique freezing temperature, viewable through the transparent enclosure of cooling element (12a-f).

To be more accurate, it is understood that typically a PCM does not have an exact freezing temperature, rather, it has a range of potential freezing temperatures within a range of approximately 2 degrees Fahrenheit in either direction.

Figure 2A:
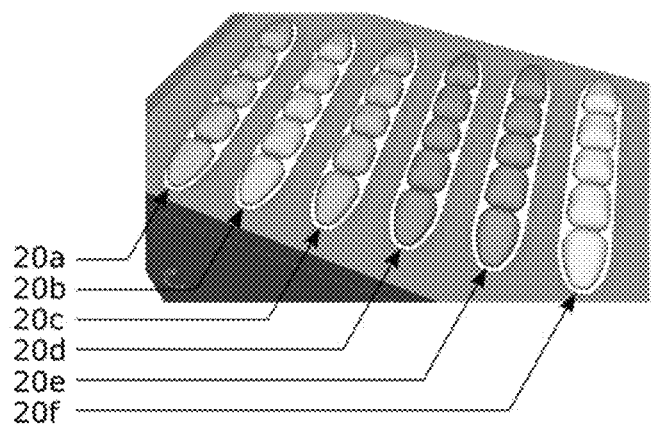
FIG. 2a shows the range of freezing temperatures of PCMs with color coded cooling elements.
Figure 2B:
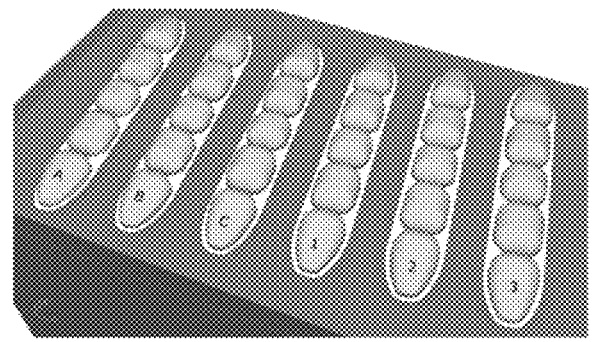
FIG. 2b shows numeral and textual symbols designated to correspond with a range of freezing temperatures.

Thus, according to one embodiment, as seen in FIG. 2a, PCMs (20a-f) have corresponding freezing temperatures of 35-40 degrees, 40-45 degrees, 45-50 degrees, 50-55 degrees, 55-60 degrees and 60-65 degrees, all Fahrenheit. In one instance, each of the colors red, orange, yellow, green, blue and indigo is indicative of one range of freezing temperatures. It should be stressed that the sample colors and temperature ranges mentioned are illustrative examples only, and a wide range of alternatives are contemplated as well. A list of colors and their corresponding range of freezing temperatures is displayed to user (14) to assist in his choosing a desired cooling element (12a-f). Additionally or alternatively, indicators such as numeral and textual symbols are designated to correspond with a range of freezing temperatures, as seen in FIG. 2b. Any or all of the above methods for indicating freezing temperature ranges are suitable for appearing on the enclosure material of cooling element (12).

The transparent enclosure material of cooling elements (12a-f) also enables user (14) to view the phase state of each color-coded PCM to indicate to the user when PCM (20a-f) are frozen and cooling elements (12a-f) are ready to be removed from cooling station (16) as well as when PCMs (20a-f) are melted and in need of cooling station (16) in order to re-freeze.

Figure 3:
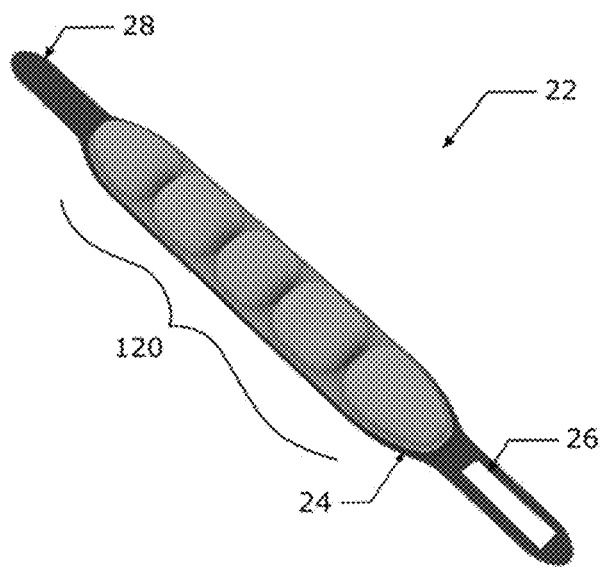
FIG. 3 shows a second aspect of the present invention, comprising of a collar pack for positioning around the neck of a user.

Referring to FIG. 3, an array of cooling elements (120), designed according to a second aspect of the first embodiment of the present invention, are integrally joined to form a collar pack (22) for positioning, for instance, around the neck of a user. In this aspect, collar pack (22) comprises an elongated array of sealed transparent cooling elements (120). Each cooling element (120) of collar pack (22) contains a PCM (not seen in the figure) with indicator according to its predetermined freezing temperature ranges. Collar pack (22) is designed to attach to a corresponding band (24) via any one of hook and loop connectors, clips and any other suitable joinable means. Longitudinal ends (26), (28) of band (24) are releasably connectable to each other via any one of hook and loop connectors, clips, drawstrings and any other suitable joinable means.

Collar pack (22) is manufactured of plastic film such as TPU, PVC, nylon, or any other suitable polymer material or combination of materials. Band (24) is manufactured of Neoprene or any foam or other suitable material to hold the collar against the neck or other part of the user.

Figure 4:
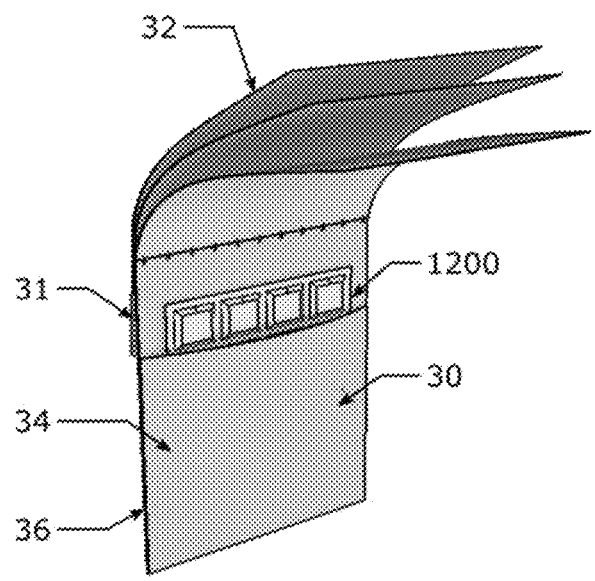
FIG. 4 shows an application of the first aspect of the present invention, comprising a seat back cooler for mounting a cooling element on the back of a seat.

Referring to FIG. 4, in a particular application, a matrix of cooling elements (1200), forming an insert, is removably insertable into a pocket (30) that is attachable to a seat back (not shown) for providing cooling to the back of the user, such as at a stadium. Pocket (30) comprises straps, clips or any other suitable means (31) for attaching to a seat back. In this aspect, one or more insulating sheets (32) are provided for removably placing between the cooling element and the user. Pocket (30) comprises a front face (34) for contact with the back of the user, and a rear face (36) for contact with the seat back. Sheets (32) are attached to pocket (30), for instance, along the upper edge like a spiral notebook as shown in the figure, or by other means such as joining with a binding piece of material, or alternatively attached to pocket (30) at one of its upper corners. Thus, in addition or as an alternative to attaching pocket (30) to a seat back as described above, it may be removably mounted by hanging sheets (32) over the seat back. In all cases the attachment is such that sheets (32) are selectively flipped between front and rear faces (34), (36) of pocket (30) as desired, or selectively insertable into pocket (30) between cooling element (1200) and front face (34), and between cooling element (12) and back face (36). Alternatively, sheets (30) are unattached to pocket (30) for selectively placing at front face (34) of pocket (30) or insertable into pocket (30) between cooling element (1200) and front face (34). Sheets (32) are selectively addable and removable from in front of cooling element (1200) depending on the user's cooling preferences, thereby adjusting the temperature level at contact with the back of the user. Rear face (34) optionally comprises one or more external pockets for storing extra cooling elements (1200).

According to one aspect of the present invention, with reference to FIGS. 1 and 2, freezing medium (18) of cooling station (16) is ice. According to another aspect, freezing medium (18) is a liquid that is maintained in a liquid state below the freezing temperature of the one or more PCMs submerged within it. For instance, freezing medium (18) is a mixture of water and salt, or water and alcohol, and is kept at a low temperature, preferably between −3 and −25 degrees Celsius in order to re-freeze cooling elements of the present invention within 3-5 minutes. Cooling elements will typically remain frozen up to 1.5 hours depending on factors such as ambient and body temperatures. In this aspect, freezing medium (18) also serves as a disinfectant to sanitize a cooling element from bacteria and other microbes that might have adhered to a cooling element from other users. In yet another aspect, freezing medium (18) comprises an environment whose temperature is below the freezing temperature of the PCM it is freezing, such as a conventional freezer. Independent alcohol-based wipes as well as other forms of disinfectant cleaners are also contemplated as part of the system of the present invention.

Figure 5:
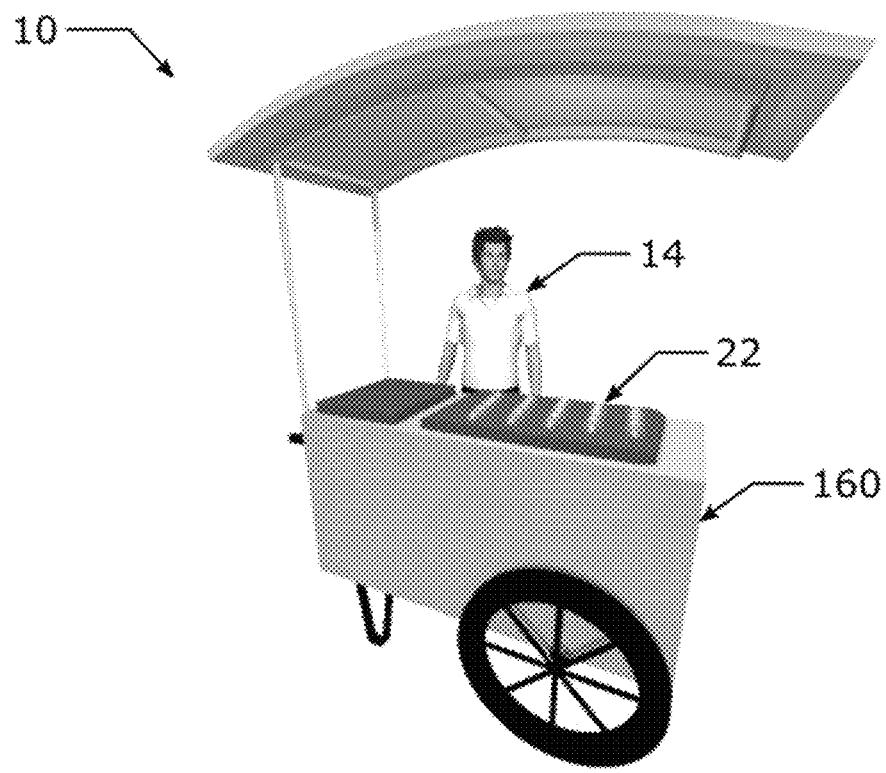
FIG. 5 shows a second aspect of the cooling station of the present invention.
Figure 5A:
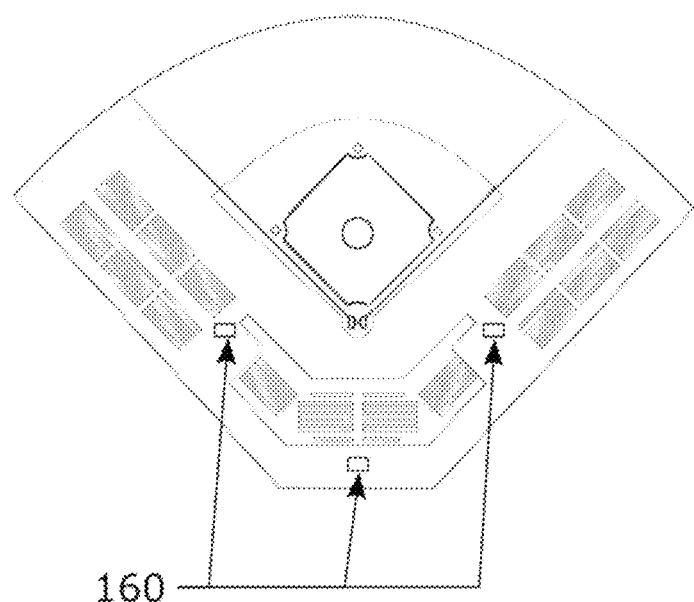
FIG. 5a shows a stadium venue having a plurality of cooling stations.

In reference to cooling station (16), according to a first aspect, it is contemplated as being easily transportable, particularly by carrying from place to place, such as a cooler shown in FIG. 1. However, it is recognized that although many of the difficulties associated with personal outdoor cooling systems are overcome according to the first aspect of cooling station (16), nevertheless, some of the difficulties described herein above would still apply. Therefore, in a second aspect, shown in FIG. 5, cooling station (160) is contemplated as being installed at a venue such as a stadium as shown in FIG. 5a, and situated at one or more predetermined locations. The venue and the one or more predetermined locations may be indoors, outdoors or a combination of the two.

For the purpose of clarity, the term, "installed at a venue" as defined herein, refers to a cooling station that is associated with a venue, independent from a particular user, such that the cooling station is situated at the venue regardless of whether a particular user is present at the venue at a particular instance in time. This includes a cooling station that is physically affixed, whether permanently or temporarily, at a predetermined location, as well as a cooling station that is movably affixed, such as via lockable rolling wheels, at a predetermined location, whereby the cooling station is designated at the predetermined location for an amount of time with the intention of servicing a plurality of independent users.

Figure 5B:
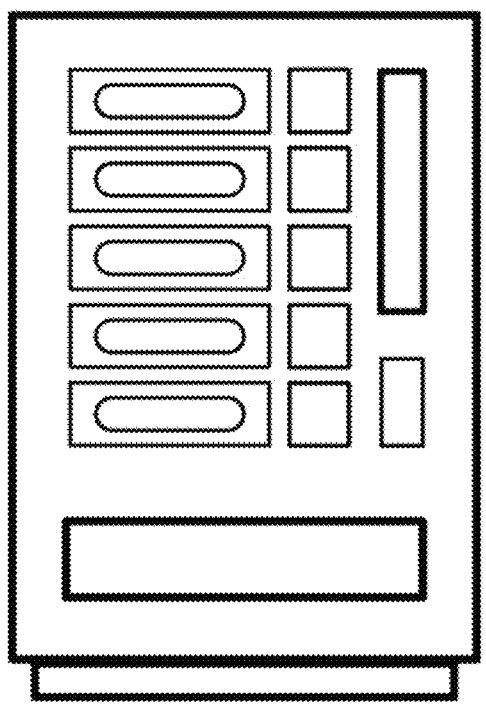
FIG. 5b shows a vending machine cooling station.

One example of a cooling station (160) installed at a venue is a vending machine such as that shown in FIG. 5b for illustrative purposes. The vending machine preferably comprises at least one slot for inserting used/melted cooling elements therein and another slot for discharging frozen cooling elements therefrom to the user. The cooling element that is discharged from the vending machine is typically the same cooling element that is inserted, or alternatively, it is a different cooling element, or alternatively user has the option of selecting between the option of receiving the same cooling element or a different one.

Another example of a cooling station (160) installed at a venue is a manned merchant stand or service desk (not shown), such as a stand-alone booth or as part of an existing store, kiosk, concession stand, service desk etc. and provides services in addition to those related to the personal cooling system of the present invention.

When installed at a venue, cooling station (160) is situated at a location where a user who would typically be spending an extended period time outdoors would be able to conveniently access it. Some examples of locations at which cooling station (160) would benefit a user are: amusement/theme parks, carnivals, stadiums and sporting events, beaches, public and private pools (e.g. swim club), hotels, hiking trails and national parks, and outdoor tourist attractions.

Typically, when cooling station (160) is installed at a venue, the services described herein are provided for a fee, although a system-wide sharing arrangement is also contemplated according to the present invention, whereby all of the services described herein are provided without monetary exchange or at least without significant monetary exchange (as a value-added service), or with monetary exchange that covers mainly or entirely just the cost of materials, or with monetary exchange for non-profit or safety purposes, or with monetary exchange for purposes of deposit, insurance and the like.

In a preferred arrangement, with reference to FIG. 5a, a plurality of cooling stations (160) installed at a venue are situated separately at an array of predetermined locations forming one or more networks of cooling stations (160) at which a user can purchase, swap and/or re-freeze a cooling element throughout the day at his convenience. Thus, for example, a network comprises cooling stations (160) strategically situated throughout an entire theme park. In another example, a network comprises cooling stations (16) situated at one or more of a hotel concierge desk, hotel pool, nearby beach and other convenient locations around and near the hotel grounds.

More broadly, the network contemplated according to the present invention comprises multiple venues, spread throughout a geographic area such as a city, country and any other sizeable region around the globe including internationally.

Figure 6:
FIG. 6 shows an app for providing information about nearby cooling stations.
Figure 7:
FIG. 7 shows a unique identifier needed for the user to access the app.

With reference to FIG. 6, according to all embodiments it is contemplated that the personal cooling system of the present invention additionally comprises an app that shows a map of all cooling stations that exist within a selected radius from the user and/or directs the user to the nearest cooling station, as well as provides desired data for a selected cooling station, such as which types and how many cooling elements they have in stock, and freezing temperature range availability. In one aspect, the app provides a user member or purchaser a unique identifier, as shown in FIG. 7 as a username and password, that entitles to recharge or swap cooling elements. The app preferably also provides the user with various subscription options, including but not limited to daily, monthly and annual membership (in various regions and/or globally); enables the user to replace, re-freeze and/or purchase cooling elements; and allow the user to order delivery of the recharged swapped cooling elements to a designated seat, address or location. Subscription options are also available without the app, via manual payments.

It is also contemplated that the present invention additionally comprises a manufacturing facility, storage location and distribution capabilities for maintaining a full stock of supplies throughout the network of cooling stations.

It is understood that the above description of the embodiments of the present invention are for illustrative purposes only, and is not meant to be exhaustive or to limit the invention to the precise form or forms disclosed, as many modifications and variations are possible. Such modifications and variations are intended to be included within the scope of the present invention as defined by the accompanying claims.

What is claimed is:

1. A personal cooling system for maintaining an individual at a preferred predetermined temperature in an outdoor environment for an extended period of time, said system comprising:
   a. at least one cooling element comprising a phase change material (PCM), and
   b. at least one cooling station comprising a medium which is a liquid that is kept in a liquid state below the freezing temperature of the PCM submerged within it, wherein said cooling elements are designed to be wearable around at least a portion of the neck of a user.

2. The personal cooling system of claim 1, wherein a freezing temperature of the PCM of at least one of the cooling elements is different from the freezing temperature of the PCM of at least one other of the cooling elements.

3. The personal cooling system of claim 1, wherein the freezing temperature of the PCM falls within a freezing temperature range, and wherein said cooling element comprises a visual indicator for indicating the freezing temperature range of said PCM.

4. The personal cooling system of claim 3, wherein the visual indicator comprises the PCM and has a color chosen to correspond to the freezing temperature range of said PCM.

5. The personal cooling system of claim 4, wherein a plurality of colors and their corresponding range of freezing temperatures is displayed to the user.

6. The personal cooling system of claim 3, wherein the visual indicator comprises an indicative symbol such as numeral and textual.

7. The personal cooling system of claim 1, wherein the cooling element is wearable on skin of the user.

8. The personal cooling system of claim 1, wherein the freezing temperature of each PCM falls within a freezing temperature range.

9. The personal cooling system of claim 1, wherein the cooling station is transportable.

10. The personal cooling system of claim 1, wherein the cooling station is installed at a venue.

11. The personal cooling system of claim 1, wherein said system comprises a network of cooling stations situated separately at predetermined locations.

12. The personal cooling system of claim 1, wherein the cooling station provides additional one or more frozen cooling elements for a fee.

13. The personal cooling system of claim 1, wherein the cooling station is comprised of a vending machine.

14. The personal cooling system of claim 1, wherein the medium further comprises one of ice, ice packs and hydratable ice sheets.

15. The personal cooling system of claim 1, wherein the medium further comprises an environment whose temperature is below the freezing temperature of the PCM it is freezing.

16. The personal cooling system of claim 1, wherein the medium is a mixture of water and one of salt and alcohol that is kept at a low temperature.

17. The personal cooling system of claim 1, wherein the medium is kept at temperature range between −3 and −25 degrees Celsius.

18. The personal cooling system of claim 1, wherein the medium serves as a disinfectant to sanitize the cooling element from bacteria and other microbes.

19. The personal cooling system of claim 1, further comprising a disinfectant for disinfecting the cooling element from bacteria and other microbes.

20. The personal cooling system of claim 1, further comprising an application for providing the individual information about nearby cooling stations.

21. The personal cooling system of claim 20, wherein the application provides the user with a unique identifier that entitles to recharge or swap cooling elements.

22. The personal cooling system of claim 1, wherein said cooling elements comprise a transparent enclosure in which the PCM is contained, for viewing the phase state of said PCM.

* * * * *